(12) United States Patent
Klyachko et al.

(10) Patent No.: US 7,785,860 B2
(45) Date of Patent: Aug. 31, 2010

(54) **METHOD FOR PRODUCING L-HISTIDINE USING *ENTEROBACTERIACEAE* BACTERIA WHICH HAS AN ENHANCED *PURH* GENE PRODUCED**

(75) Inventors: Elena Vitalievna Klyachko, Moscow (RU); Rustem Saidovich Shakulov, Moscow (RU); Yuri Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 365 days.

(21) Appl. No.: 10/927,041

(22) Filed: Aug. 27, 2004

(65) Prior Publication Data

US 2005/0048631 A1  Mar. 3, 2005

(30) Foreign Application Priority Data

Aug. 29, 2003  (RU) ............... 2003126290

(51) Int. Cl.
*C12N 1/20* (2006.01)
*C12P 13/24* (2006.01)

(52) U.S. Cl. .................. 435/252.3; 435/107

(58) Field of Classification Search ........... None
See application file for complete search history.

(56) References Cited

U.S. PATENT DOCUMENTS

| | | | |
|---|---|---|---|
| 4,278,765 A | 7/1981 | Debabov et al. | 435/172 |
| 5,661,012 A | 8/1997 | Sano et al. | 435/115 |
| 6,040,160 A | 3/2000 | Kojima et al. | 435/115 |
| 6,297,031 B1 | 10/2001 | Debabov et al. | 435/115 |
| 6,653,111 B2 | 11/2003 | Debabov et al. | 435/115 |
| 2001/0049126 A1 | 12/2001 | Livshits et al. | 435/106 |
| 2002/0102665 A1* | 8/2002 | Kino et al. | 435/106 |
| 2004/0038380 A1 | 2/2004 | Debabov et al. | 435/115 |
| 2004/0132165 A1 | 7/2004 | Akhverdian et al. | 435/252 |
| 2004/0229320 A1 | 11/2004 | Stoynova et al. | 435/106 |
| 2004/0229321 A1 | 11/2004 | Savrasova et al. | 435/106 |

FOREIGN PATENT DOCUMENTS

JP  56-018596 A  2/1981

OTHER PUBLICATIONS

Aiba et al. (1989) The Journal of Biological Chemistry, vol. 264(35), pp. 21239-21246.*
Herrero et al. (1990) Journal of Bacteriology, vol. 172(11), pp. 6557-6567.*
Brilli et al. (2004) Journal of Molecular Evolution, vol. 58, pp. 225-237.*
Rayl et al. (1996) Journal of Biological Chemistry, vol. 271(4), pp. 2225-2233.*
Meyers et al., 1975, Journal of Bacteriology, vol. 124, pp. 1227-1235.*
Moyed, 1961, The Journal of Biological Chemistry, vol. 236, pp. 2261-2267.*

(Continued)

*Primary Examiner*—David J Steadman
*Assistant Examiner*—Alexander D Kim
(74) *Attorney, Agent, or Firm*—Shelly Guest Cermak; Cermak Nakajima LLP (57) ABSTRACT

A method is provided for producing L-histidine using bacterium of the Enterobacteriaceae family wherein the L-amino acid productivity of said bacterium is enhanced by enhancing an activity of the AICAR transformylase-IMP cyclohydrolase encoded by the purH gene.

10 Claims, 2 Drawing Sheets

OTHER PUBLICATIONS

Cho et al., Crystal Structure of ATP Phosphoribosyltransferase from *Mycobacterium tuberculosis*, The Journal of Biological Chemistry, 2003, vol. 278, pp. 8333-8339.*

Guo et al., Protein tolerance to random amino acid change, 2004, Proc. Natl. Acad. Sci. USA 101: 9205-9210.*

Lazar et al., Transforming Growth Factor alpha: Mutation of Aspartic Acid 47 and Leucine 48 Results in Different Biological Activities, 1988, Mol. Cell. Biol. 8:1247-1252.*

Hill et al., Functional Analysis of Cerserved Histidines in ADP-Glucose Pyrophosphorylase from *Escherichia coli*, 1998, Biochem. Biophys. Res. Comm. 244:573-577.*

Allen et al., Metabolic Flux in Both the Purine Mononucleotide and Histidine Biosynthetic Pathways Can Influence Synthesis of the Hydroxymethyl Pyrimidine Moiety of Thiamine in *Salmonella enterica*., Journal of Bacteriology, 2002, vol. 184, pp. 6130-6137.*

Holmes et al., Cloning and Characterization of Methenyltetrahydrofolate Synthetase from *Saccharomyces cerevisiae*., The Journal of Biological Chemistry, 2002, vol. 277, pp. 20205-20213.*

Aiba, A., et al., "Nucleotide Sequence Analysis of Gene *purH* and *purD* Involved in the *de Novo* Purine Nucleotide Biosynthesis of *Escherichia coli*," J. Biol. Chem. 1989;264(35):21239-21246.

Petersen, C., et al., "The Cryptic Adenine Deaminase Gene of *Escherichia coli*," J. Biol. Chem. 2002;277(35):31373-31380.

Rayl, E. A., et al., "The Human *purH* Gene Product, 5-Aminoimidazole-4-carboxamide Ribonucleotide Formyltransferase/IMP Cyclohydrolase," J. Biol. Chem. 1996;271(4):2225-2233.

Tibbetts, A. S., et al., "Characterization of Two 5-Aminoimidazole-4-carboxamide Ribonucleotide Transformylase/Inosine Monophosphate Cyclohydrolase Isozymes from *Saccharomyces cerevisiae*," J. Biol. Chem. 2000;275(27):20920-20927.

Partial European Search Report for EP. App. No. 04020392 (Mar. 3, 2006).

Neidhardt F. C., et al., "*Escherichia coli* and *Salmonella*; Cellular and Molecullar Biology; Second Edition", ASM Press, American Society for Microbiology, 1325 Massachusetts Ave., Washington, D.C., pp. 561-579 (1996).

U.S. Appl. No. 09/684,618, filed Oct. 10, 2000, Gusyatiner et al.
U.S. Appl. No. 10/984,821, filed Nov. 10, 2004, Klyachko et al.
U.S. Appl. No. 11/002,072, filed Dec. 3, 2004, Akhverdian et al.
U.S. Appl. No. 10/892,113, filed Jul. 16, 2004, Klyachko et al.
U.S. Appl. No. 10/862,424, filed Jun. 8, 2004, Imaizumi et al.
U.S. Appl. No. 11/059,686, filed Feb. 17, 2005, Marchenko et al.

* cited by examiner

METHOD FOR PRODUCING L-HISTIDINE USING *ENTEROBACTERIACEAE* BACTERIA WHICH HAS AN ENHANCED *PURH* GENE PRODUCED

BACKGROUND OF THE INVENTION

1. Field of the invention

The present invention relates to biotechnology, and specifically to a method for producing an L-amino acid, such as L-histidine, by fermentation. The present invention specifically relates to a gene derived from an *Escherichia coli* bacterium. The gene is useful for improving production of L-histidine.

2. Description of the Related Art

Conventionally, L-amino acids have been industrially produced by fermentation utilizing strains of microorganisms obtained from natural sources or mutants of the same modified to enhance L-amino acid productivity.

Many techniques have been reported regarding enhancement of L-amino acid production, for example, by transformation of a microorganism by recombinant DNA (see, for example, U.S. Pat. No. 4,278,765). These techniques are based on increasing the activities of the enzymes involved in amino acid biosynthesis and/or desensitizing target enzymes from feedback inhibition by the produced L-amino acid (see, for example, Japanese Laid-open application No. 56-18596 (1981), WO 95/16042 or U.S. Pat. Nos. 5,661,012 and 6,040,160).

In the L-histidine biosynthetic pathway, imidazoleglycerol phosphate synthase encoded by the hisH and hisF genes catalyzes reaction whereby an intermediate compound, 5'-phosphoribosyl-4-carboxamide-5-aminoimidazole (AICAR), is released. At the same time, the initial reaction in the L-histidine biosynthetic pathway is catalyzed by the HisG protein and involves a displacement on C-1 of phosphoribosylpyrophosphate (PRPP) by N-1 of the purine ring of adenosine triphosphate (ATP). However, AICAR is not only released upon histidine biosynthesis but it is also the precursor in the biosynthesis of purines and, consequently, purine nucleosides and nucleotides, such as AMP and ATP. So, recycling of AICAR to AMP is an important process in L-histidine production.

The purH gene encodes a bifunctional enzyme having AICAR transformylase activity ((also known as 5'-phosphoribosyl-4-carboxamide-5-aminoimidazole transformylase) [EC 2.1.2.3] and IMP cyclohydrolase activity [EC 3.5.4.10]. The latter activity catalyzes the penultimate and final steps in the de novo synthesis of inosine monophosphate (IMP) (*Escherichia coli* and *Salmonella*, Second Edition, Editor in Chief: F. C. Neidhardt, ASM Press, Washington D.C., 1996).

There have been no reports to date, however, describing enhancement of the dual activities of AICAR transformylase-IMP cyclohydrolase for the purpose of improving L-histidine production using strains of the Enterobacteriaceae family.

SUMMARY OF THE INVENTION

An object of the present invention is to develop an L-histidine-producing microorganism strain which has enhanced productivity of L-histidine. It is a further object of the present invention to provide a method for producing L-histidine using such a strain.

It is a further object of the present invention to provide an L-histidine-producing bacterium of the Enterobacteriaceae family having an enhanced activity of one or more enzymes involved in conversion of 5'-phosphoribosyl-4-carboxamide-5-aminoimidazole (AICAR) to inosine-5'-monophosphate (IMP).

It is a further object of the present invention to provide the bacterium as described above, wherein the bacterium has enhanced activity of AICAR transformylase-IMP cyclohydrolase.

It is a further object of the present invention to provide the bacterium as described above, wherein the bacterium belongs to the genus *Escherichia*.

It is a further object of the present invention to provide the bacterium as described above, wherein the activity of AICAR transformylase-IMP cyclohydrolase is enhanced by increasing the expression amount of an AICAR transformylase-IMP cyclohydrolase gene.

It is a further object of the present invention to provide the bacterium as described above, wherein the activity of AICAR transformylase-IMP cyclohydrolase is increased by a method selected from the group consisting of (a) increasing the copy number of the AICAR transformylase-IMP cyclohydrolase gene and (b) modifying an expression control sequence of the gene so that the expression of the gene is enhanced.

It is a further object of the present invention to provide the bacterium as described above, wherein the copy number is increased by transformation of the bacterium with a multi-copy vector harboring the AICAR transformylase-IMP cyclohydrolase gene.

It is a further object of the present invention to provide the bacterium as described above, wherein the copy number is increased by integration of additional copies of the AICAR transformylase-IMP cyclohydrolase gene into chromosome of the bacterium.

It is a further object of the present invention to provide the bacterium as described above, wherein the AICAR transformylase-IMP cyclohydrolase gene is derived from a bacterium belonging to the genus *Escherichia*.

It is a further object of the present invention to provide the bacterium as described above, wherein the AICAR transformylase-IMP cyclohydrolase gene encodes a protein selected from the group consisting of:

(A) a protein comprising the amino acid sequence shown in SEQ ID NO: 2;

(B) a protein variant of the amino acid sequence shown in SEQ ID NO: 2, wherein said variant has an activity of AICAR transformylase-IMP cyclohydrolase.

Hereinafter, the proteins as defined in the above (A) or (B) are referred to as "proteins of the present invention".

It is a further object of the present invention to provide the bacterium as described above, wherein the AICAR transformylase-IMP cyclohydrolase gene is selected from the group consisting of:

(a) a DNA which comprises a nucleotide sequence of nucleotides 1 to 1590 in SEQ ID NO: 1; and (b) a DNA which is hybridizable with a nucleotide sequence of nucleotides 1-1590 in SEQ ID NO: 1 or a probe which can be prepared from the nucleotide sequence under stringent conditions and encodes a protein having an activity of AICAR transformylase-IMP cyclohydrolase.

It is a further object of the present invention to provide the bacterium as described above, wherein the stringent conditions are conditions in which washing is performed at 60° C. for 15 minutes, at a salt concentration corresponding to 1×SSC and 0.1% SDS.

It is a further object of the present invention to provide a method for producing L-histidine, which comprises cultivating the bacterium as described above in a culture medium, and collecting the L-histidine from the culture medium.

It is a further object of the present invention to provide the method as described above, wherein the bacterium has enhanced expression of genes for histidine biosynthesis.

DETAILED DESCRIPTION OF THE INVENTION

The aforementioned objects were achieved by identifying that the protein products of the purH gene, AICAR transformylase (5'-phosphoribosyl-4-carboxamide-5-aminoimidazole transformylase) [EC 2.1.2.3] and IMP cyclohydrolase [EC 3.5.4.10], are not involved in the biosynthetic pathway of the target L-amino acid, but can enhance L-histidine production when additional copies are introduced into the cells of the respective L-amino acid producing strain. Thus, the present invention has been completed.

The present invention will be explained in detail below.

The bacterium of the present invention is an L-histidine producing bacterium of the Enterobacteriaceae family having increased activity of one or more of the enzymes involved in conversion of 5'-phosphoribosyl-4-carboxamide-5-aminoimidazole (AICAR) to inosine-5'-monophosphate (IMP). Specifically, the bacterium of the present invention is an L-histidine-producing bacterium of the Enterobacteriaceae family, wherein L-histidine production by the bacterium is enhanced by increasing an activity of the protein of the present invention in the bacterium as compared to the wild-type bacterium. More specifically, the bacterium of the present invention is an L-histidine-producing bacterium belonging to the genus Escherichia, wherein L-histidine production by the bacterium is enhanced by increasing an activity of the protein of the present invention, namely AICAR transformylase-IMP cyclohydrolase, in the bacterium. More specifically, the bacterium of present invention harbors chromosomal or plasmid DNA which includes the purH gene, and has an enhanced ability to produce L-histidine by virtue of overexpression of the purH gene.

"L-histidine producing-bacterium" means a bacterium, which has an ability to produce and secrete L-histidine into a medium, when the bacterium of the present invention is cultured in the medium. The L-histidine-producing ability may be imparted, for example by transformation of bacterium by recombinant DNA enhancing expression of L-histidine biosynthesis genes, or enhanced by breeding, for example, by selection on structural analogues of L-histidine—D,L-1,2,4-triazole-3-alanine—resulting in the bacterium harboring ATP phosphoribosyl transferase, the key enzyme of L-histidine biosynthesis (encoded by hisG gene) with desensitized feedback inhibition by L-histidine (Russian patents 2003677 and 2119536) and able to produce L-histidine. The term "L-histidine-producing bacterium" as used herein may also mean a bacterium, which is able to produce and secrete L-histidine into a culture medium in an amount larger than a wild-type or parental strain, and preferably means the microorganism which is able to produce and secrete L-histidine into a medium in an amount of not less than 0.5 g/L, more preferably not less than 1.0 g/L.

The Enterobacteriaceae family of bacteria includes bacteria belonging to the genera Escherichia, Erwinia, Providencia and Serratia. The genus Escherichia is preferred.

The phrase "a bacterium belonging to the genus Escherichia" means that the bacterium which is classified as the genus Escherichia according to the classification known to a person skilled in the art of microbiology. A microorganism belonging to the genus Escherichia as used in the present invention includes, but is not limited to Escherichia coli (E. coli).

The phrase "enzymes involved in the conversion of 5'-phosphoribosyl-4-carboxamide-5-aminoimidazole (AICAR) to inosine-5'-monophosphate (IMP)" includes enzymes having activities of AICAR transformylase and IMP cyclohydrolase. Generally, both enzymatic activities are represented in one fused protein in the native organisms. But these enzymatic activities represented in separate non-fused proteins is also encompassed by the present invention. The present invention also encompasses a bacterium that has enhanced activity of only one of the enzymes, preferably AICAR transformylase.

The phrase "activity of AICAR transformylase-IMP cyclohydrolase" means an activity to catalyze the reaction of transferring formyl moiety from 10-formyltetrahydrofolate to AICAR, followed by formation of purine cycle yielding inosine 5'-monophosphate (IMP). The activity of the AICAR transformylase-IMP cyclohydrolase may be measured by the method described by, for example, Ni, L. et al (Gene, 106(2): 197-205 (1991)) using AICAR and (6-R)N10-formyltetrahydrofolate as substrates. Also the activity of the AICAR transformylase-IMP cyclohydrolase may be exhibited by mutation complementation technique (see, for example Aiba, A. and Mizobuchi, K., J. Biol. Chem. 264(35): 21239-46 (1989)).

The phrase "having enhanced activity of an enzyme" means that the enzyme activity per cell is higher than that of a non-modified strain, for example, a wild-type strain. For example, cells in which the number of AICAR transformylase-IMP cyclohydrolase molecules per cell increases, cells in which specific activity per AICAR transformylase-IMP cyclohydrolase molecule increases, and so forth are encompassed. Furthermore, the wild-type strain that can serve as an object for comparison includes, for example, the Escherichia coli K-12. As a result of the enhancement of intracellular activity of AICAR transformylase-IMP cyclohydrolase, L-histidine accumulation in a medium is increased.

Enhancement of AICAR transformylase-IMP cyclohydrolase activity in a bacterial cell can be achieved by enhancement of expression of a gene encoding AICAR transformylase-IMP cyclohydrolase. Genes encoding AICAR transformylase-IMP cyclohydrolase derived from bacteria of the Enterobacteriaceae family and/or genes derived from other bacteria, such as coryneform bacteria, can be used. Genes derived from bacteria belonging to the genus Escherichia are preferred.

As the gene encoding AICAR transformylase-IMP cyclohydrolase of Escherichia coli (EC numbers 2.1.2.3 and 3.5.4.10, respectively), the purH gene has already been reported (nucleotide numbers 4203521 to 4205110 in the sequence of GenBank accession NC_000913.1, gi: 16127994). Therefore, the purH gene can be obtained by PCR (polymerase chain reaction; refer to White, T. J. et al., Trends Genet., 5, 185 (1989)) utilizing primers based on the nucleotide sequence of the gene. Genes encoding AICAR transformylase-IMP cyclohydrolase of other microorganisms can be obtained in a similar manner.

An example of the purH gene derived from Escherichia coli includes a DNA which encodes the following protein (A) or (B):

a protein, which comprises the amino acid sequence shown in SEQ ID NO:2; or (B) a protein variant of the amino acid sequence shown in SEQ ID NO: 2, and which has an activity of AICAR transformylase-IMP cyclohydrolase.

The DNA encoding proteins of the present invention includes a DNA encoding protein variants, possibly having deletions, substitutions, insertions or additions of one or several amino acids in one or more positions on the protein (A) as long as such changes do not result in loss of the protein's activity. The number of "several" amino acids differs depending on the position of amino acid residues in the three-dimensional structure of the protein and the type of the amino acids. However it preferably means between 2 to 50, more preferably between 2 to 20, and most preferably between 2 to 10 for the protein (A). This is because of the following reason. Some amino acids have high homology to one another and the difference in such an amino acid does not greatly affect the three dimensional structure of the protein and its activity. Therefore, the protein (B) may be one which has homology of not less than 30 to 50%, preferably 50 to 70%, more preferably 70 to 90%, more preferably not less than 90%, and most preferably not less than 95% with respect to the entire amino acid sequence of AICAR transformylase-IMP cyclohydrolase, and which has the activity of AICAR transformylase-IMP cyclohydrolase.

To evaluate the degree of protein or DNA homology, known calculation methods can be used, such as BLAST search, FASTA search and CrustalW.

BLAST (Basic Local Alignment Search Tool) is the heuristic search algorithm employed by the programs blastp, blastn, blastx, megablast, tblastn, and tblastx; these programs ascribe significance to their findings using the statistical methods of Karlin, Samuel and Stephen F. Altschul ("Methods for assessing the statistical significance of molecular sequence features by using general scoring schemes". Proc. Natl. Acad. Sci. USA, 1990, 87:2264-68; "Applications and statistics for multiple high-scoring segments in molecular sequences". Proc. Natl. Acad. Sci. USA, 1993, 90:5873-7). FASTA search method described by W. R. Pearson ("Rapid and Sensitive Sequence Comparison with FASTP and FASTA", Methods in Enzymology, 1990 183:63-98). ClustalW method described by Thompson J. D., Higgins D. G. and Gibson T. J. ("CLUSTAL W: improving the sensitivity of progressive multiple sequence alignment through sequence weighting, position-specific gap penalties and weight matrix choice", Nucleic Acids Res. 1994, 22:4673-4680).

Changes to AICAR transformylase-IMP cyclohydrolase such as those described above are typically conservative changes so as to maintain the activity of AICAR transformylase-IMP cyclohydrolase. Substitution changes include those in which at least one residue in the amino acid sequence has been removed and a different residue inserted in its place. Examples of amino acids which may be substituted for an original amino acid in a AICAR transformylase-IMP cyclohydrolase protein and which are regarded as conservative substitutions include: Ala substituted with ser or thr; arg substituted with gin, his, or lys; asn substituted with glu, gin, lys, his, asp; asp substituted with asn, glu, or gin; cys substituted with ser or ala; gin substituted with asn, glu, lys, his, asp, or arg; glu substituted with asn, gin, lys, or asp; gly substituted with pro; his substituted with asn, lys, gin, arg, tyr; ile substituted with leu, met, val, phe; leu substituted with ile, met, val, phe; lys substituted with asn, glu, gin, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

The DNA encoding substantially the same protein as the protein defined in (A), such as a protein variant, may be obtained by, for example, modification of nucleotide sequence encoding the protein defined in (A) using site-directed mutagenesis so that one or more amino acid residue will be deleted, substituted, inserted or added. Such modified DNA can be obtained by conventional methods using treatment with reagents and conditions generating mutations. Such treatment includes treatment the DNA encoding proteins of present invention with hydroxylamine or treatment the bacterium harboring the DNA with UV irradiation or reagent such as N-methyl-N'-nitro-N-nitrosoguanidine or nitrous acid.

The DNA encoding proteins of the present invention include variants which can be found in different strains of bacteria belonging to the genus *Escherichia* by virtue of natural diversity. DNA encoding such variants can be obtained by isolating the DNA which hybridizes to the purH gene or a part thereof under stringent conditions, and which encodes the protein having an activity of AICAR transformylase-IMP cyclohydrolase. The term "stringent conditions" may include conditions under which a so-called specific hybrid is formed, and a non-specific hybrid is not formed. For example, stringent conditions include conditions under which DNAs having high homology, for instance DNAs having homology not less than 70%, preferably not less than 80%, more preferably not less than 90%, most preferably not less than 95% to each other, are able to hybridize. Alternatively, stringent conditions may include conditions which are typical washing conditions for Southern hybridization, e.g., 60° C., 1×SSC, 0.1% SDS, preferably 0.1×SSC, 0.1% SDS. Duration of washing procedure depends on the type of membrane used for blotting and, as a rule, is recommended by manufacturer. For example, recommended duration of washing the Hybond™ N+nylon membrane (Amersham) under stringent conditions is 15 minutes. As a probe for the DNA that encodes variants and hybridizes with purH gene, a partial sequence of the nucleotide sequence of SEQ ID NO: 1 can also be used. Such a probe may be prepared by PCR using oligonucleotides based on the nucleotide sequence of SEQ ID NO: 1 as primers, and a DNA fragment containing the nucleotide sequence of SEQ ID NO: 1 as a template. When a DNA fragment of about 300 bp in length is used as the probe, the washing conditions for the hybridization can be, for example, 50° C., 2×SSC, and 0.1% SDS.

Transformation of bacterium with a DNA encoding a protein means introduction of the DNA into a bacterium, for example by conventional methods to increase the expression of the gene encoding the protein of present invention and to enhance the activity of the protein in the bacterium.

The bacterium of the present invention also includes one wherein the activity of the protein of the present invention is enhanced by transformation of said bacterium with DNA encoding the protein as defined previously in (A) or (B), or by alteration of an expression regulation or control sequence of said DNA on the chromosome of the bacterium.

The DNA, which is used for modification of the bacterium of the present invention may encode a protein having an activity of the AICAR transformylase-IMP cyclohydrolase. More specifically, the DNA may be the purH gene. The purH gene can be obtained by, for example, PCR using primers based on the nucleotide sequence shown in SEQ ID No: 1.

The methods of the enhancement of gene expression include increasing the gene copy number. Introduction of a gene into a vector that is able to function in a bacterium belonging to the genus *Escherichia* increases the copy number of the gene. Multi-copy vectors can be preferably used, and include pBR322, pUC19, pBluescript KS+, pACYC177, pACYC184, pAYC32, pMW119, pET22b and the like.

Enhancement of gene expression can be achieved by introducing multiple copies of the gene into bacterial chromosome by, for example, homologous recombination methods and the like.

Alternatively, the enhancement of gene expression can be achieved by placing the DNA of the present invention under the control of more potent promoter rather than the native promoter. Strength of a promoter is defined by frequency of acts of the RNA synthesis initiation. Methods for evaluation the strength of promoter and an examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5, 2987-2994). For example, the $P_R$ promoter is known to be a potent constitutive promoter. Other known potent promoters are the $P_L$ promoter, lac promoter, trp promoter, trc promoter, of lambda phage and the like.

Enhancing translation can be achieved by introducing the more efficient Shine-Dalgarno sequence (SD sequence) into the DNA of the present invention. The SD sequence is a region upstream of the start codon of mRNA which interacts with the 16S RNA of ribosome (Shine J. and Dalgarno L., Proc. Natl. Acad. Sci. USA, 1974, 71, 4, 1342-6).

Use of potent promoters can be combined with multiplication of gene copies.

Methods for preparation of chromosomal DNA, hybridization, PCR, preparation of plasmid DNA, digestion and ligation of DNA, transformation, selection of an oligonucleotide as a primer and the like include typical methods well known to one of ordinary skill in the art. Such methods are described in Sambrook, J., and Russell D., "Molecular Cloning A Laboratory Manual, Third Edition", Cold Spring Harbor Laboratory Press (2001) and the like.

The bacterium of the present invention can be obtained by introduction of the aforementioned DNAs into a bacterium which inherently has the ability to produce L-histidine. Alternatively, the bacterium of present invention can be obtained by imparting the ability to produce L-histidine to the bacterium already harboring the DNAs.

As a parent strain which is to be enhanced in activity of the protein of the present invention, bacteria belonging to the genus *Escherichia* having L-histidine producing ability, the L-histidine producing bacterium strains belonging to the genus *Escherichia*, such as *E. coli* strain 24 (VKPM B-5945, Russian patent 2003677); *E. coli* strain 80 (VKPM B-7270, Russian patent 2119536); *E. coli* strains NRRL B-12116-B112121 (U.S. Pat. No. 4,388,405); *E. coli* strains H-9342 (FERM BP-6675) and H-9343 (FERM BP-6676) (U.S. Pat. No. 6,344,347); *E. coli* strain H-9341 (FERM BP-6674) (European patent application 1085087A2); *E. coli* strain AI80/pFM201 (U.S. Pat. No. 6,258,554) and the like are encompassed.

It is desired that the L-histidine producing bacterium be further modified to have enhanced expression of L-histidine biosynthesis genes. Genes effective for L-histidine biosynthesis include the hisG gene and genes of the hisBHAFI operon. The hisG gene encoding an ATP phosphoribosyl transferase for which feedback inhibition by L-histidine is desensitized (Russian patents 2003677 and 2119536) is preferred.

The method of present invention includes production of L-histidine, comprising the steps of cultivating the bacterium of the present invention in a culture medium, allowing the L-histidine to be produced, and collecting the secreted and accumulated L-histidine from the culture medium.

In the present invention, the cultivation, collection and purification of L-histidine from the medium and the like may be performed by conventional fermentation methods for production of an amino acid using a microorganism.

A medium used for culture may be either a synthetic medium or a natural medium, so long as the medium includes a carbon source and a nitrogen source and minerals and, if necessary, appropriate amounts of nutrients which the microorganism requires for growth.

The carbon source may include various carbohydrates such as glucose and sucrose, and various organic acids. Depending on the mode of assimilation of the used microorganism, alcohol including ethanol and glycerol may be used.

As the nitrogen source, various ammonium salts such as ammonia and ammonium sulfate, other nitrogen compounds such as amines, a natural nitrogen source such as peptone, soybean-hydrolysate and digested fermentative microorganism are used.

As minerals, potassium monophosphate, magnesium sulfate, sodium chloride, ferrous sulfate, manganese sulfate, calcium chloride, and the like are used. Some additional nutrient can be added to the medium if necessary. For instance, if the microorganism requires proline for growth (proline auxotrophy) the sufficient amount of proline can be added to the medium for cultivation.

The cultivation is performed preferably under aerobic conditions such as a shaking culture, and stirring culture with aeration, at a temperature of 20 to 42° C., preferably 37 to 40° C. The pH of the culture is usually between 5 and 9, preferably between 6.5 and 7.2. The pH of the culture can be adjusted with ammonia, calcium carbonate, various acids, various bases, and buffers. Usually, an 1 to 5-day cultivation leads to the secretion and accumulation of the target L-amino acid in the liquid medium.

After cultivation, solids such as cells can be removed from the liquid medium by centrifugation or membrane filtration, and then the target L-amino acid can be collected and purified by ion-exchange, concentration and crystallization methods.

The present invention will be more concretely explained with reference to the following non-limiting Examples. In the Examples, an amino acid is of L-configuration unless otherwise noted.

Example 1

Cloning the purH Gene from *E. coli*

The entire nucleotide sequence of *E. coli* strain K-12 has been reported (Science, 277, 1453-1474, 1997). Based on this reported nucleotide sequence, the primers depicted in SEQ ID No. 3 (primer 1) and No. 4 (primer 2) for amplification of purH gene were synthesized. Primer 1 contains a HindIII recognition site introduced at the 5' thereof. Primer 2 contains a XbaI recognition site introduced at the 5'-end thereof.

Figure 1:
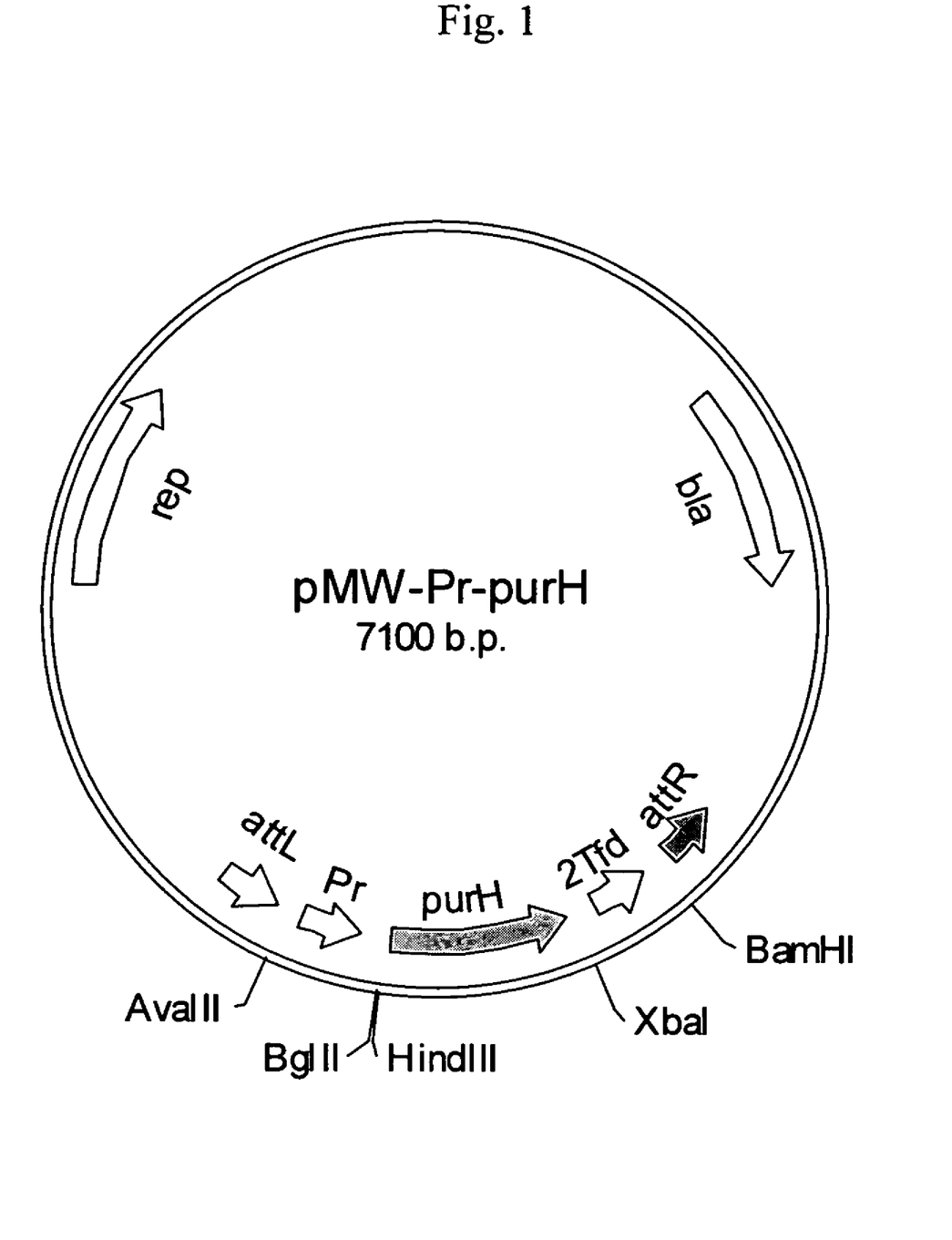
FIG. 1 shows the structure of the PMW-P$_R$-purH plasmid.

The chromosomal DNA of *E. coli* K12 which was used as template for PCR was prepared by an ordinary method. PCR was carried out on "Applied Biosystems GeneAmp PCR System 2400" under the following conditions: initial DNA denaturation at 95° C. for 5 min; then 30 cycles of denaturation at 95° C. for 30 sec, annealing at 55° C. for 60 sec and elongation at 72° C. for 120 sec; the final polymerization for 7 min at 72° C. using Taq polymerase (Fermentas, Lithuania). The obtained PCR fragment containing the purH gene without a promoter was treated with HindIII and XbaI and inserted so it was under the control of the $P_R$ promoter in the integrative vector, pMW119-$P_R$, which had been previously treated with the same enzymes. Vector pMW119-$P_R$ was constructed from commercially available vector pMW119 by insertion of $P_R$ promoter from phageλ and attR and attL sites necessary for further Mu-integration. Thus, plasmid PMW-P$_R$-purH was obtained (see FIG. 1).

Example 2

Effect of Enhanced Expression of purH Gene on Histidine Production

Two histidine producing strains were constructed. One strain harbored the plasmid with the purH gene and the other was a plasmidless strain containing additional copies of the purH gene integrated into bacterial chromosome. The histidine-producing *E. coli* strain 80 was used as the parental strain for transformation with plasmid pMW-P$_R$-purH and for integration of purH gene into the bacterial chromosome. The strain 80 has been described in Russian patent 2119536 and deposited in the Russian National Collection of Industrial Microorganisms (Russia, 113545 Moscow, 1$^{st}$ Dorozhny proezd, 1) on Oct. 15, 1999 under accession number VRPM B-7270. Then, it was converted to an international deposit under the provisions of the Budapest Treaty on Jul. 12, 2004.

Transformation of strain 80 with plasmid PMW-P$_R$-purH was performed by an ordinary method, described in Sambrook, J., and Russell D., "Molecular Cloning A Laboratory Manual, Third Edition", Cold Spring Harbor Laboratory Press (2001), yielding strain 80/PMW-P$_R$-purH.

Figure 2:
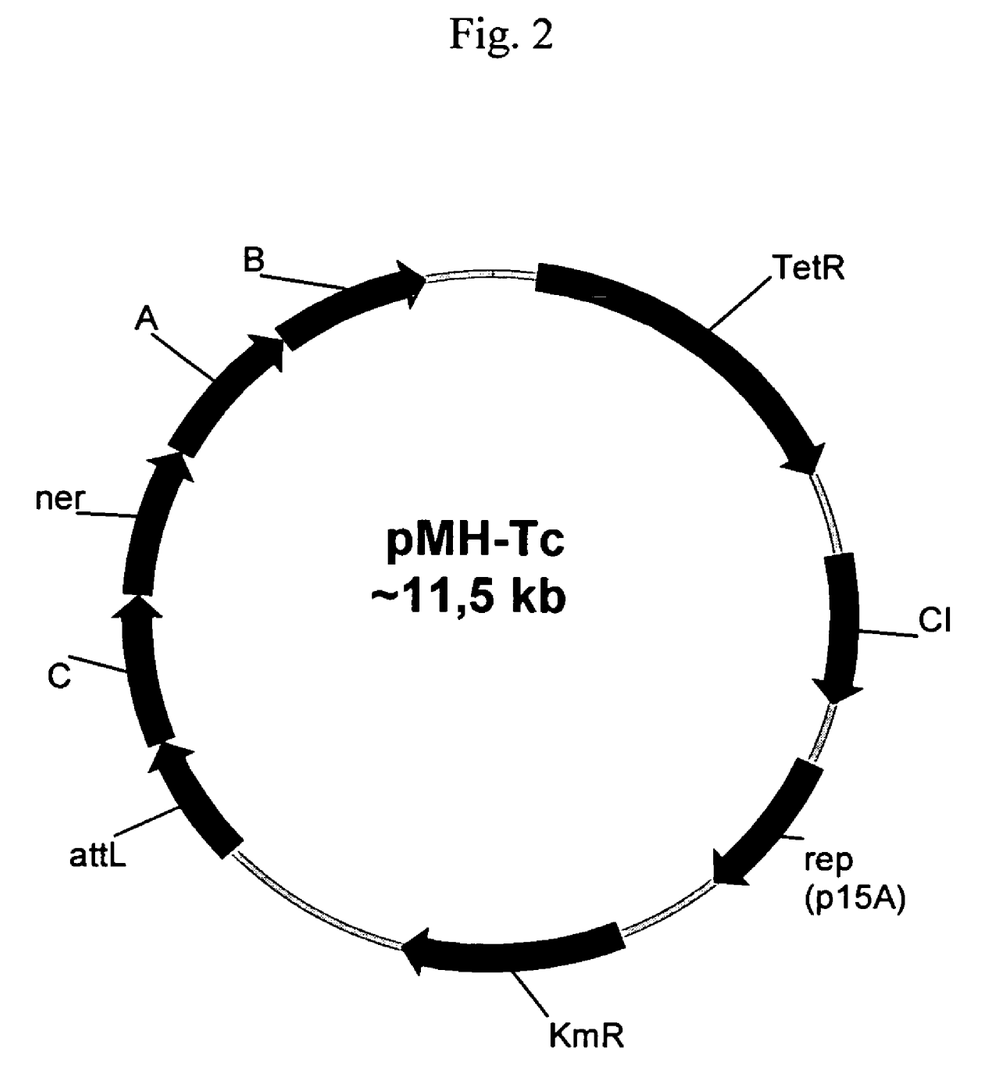
FIG. 2 shows the structure of the pMH-Tc helper plasmid.

Integration of purH gene into chromosome of strain 80 was performed in two steps. At the first step the histidine-producing strain 80 was transformed with the pMH-Tc helper plasmid which contains replicon rep(p15A), transposase gene (genes cts62, ner, A, B from phage Mu-cts), cI—thermosensitive lambda phage repressor (cI$_{857}$) and which harbours Tet$^R$ marker from plasmid pBR322 (see FIG. 2). At the second stage the resulting strain was transformed with the plasmid PMW-P$_R$-purH. For integration of the purH gene into chromosome, the heat-shocked cells which were treated at 42° C. for 1 minute to perform the transformation with the PMW-P$_R$-purH were transferred to 1 ml of L-broth, incubated at 44° C. for 20 minutes, at 37° C. for 40 minutes, and then the cells were spreaded onto L-agar containing 10 μg/ml of tetracycline and 100 μg/ml of ampicillin selecting the cells harboring both plasmids. Colonies which appeared within 48 hours at 30° C. were inoculated in 1 ml of L broth and incubated for 72 hours at 42° C. in tubes. About 10 colonies from each tube were checked for ampicillin and tetracycline resistance. Colonies sensitive to both antibiotics were tested for the presence of additional copies of the purH gene in the chromosome by PCR using primer 1 (SEQ ID No 3) and primer 3 (SEQ ID No 5). Primer 3 contains a sequence complementary to the attR site of phage Mu. For that purpose, a freshly isolated colony was suspended in 50 μl of water and then 1 μl was used in PCR. PCR conditions were as follows: initial DNA denaturation at 95° C. for 5 minutes; then 30 cycles of denaturation at 95° C. for 30 sec, annealing at 56° C. for 60 sec and elongation at 72° C. for 120 sec; the final polymerization at 72° C. for 7 min. Upon testing, a few antibiotic-sensitive colonies contained the necessary 2,000 bp DNA fragment. Thus strain 80::P$_R$-purH was obtained.

Strains 80, 80/PMW-P$_R$-purH and 80::P$_R$-purH were cultivated in L broth with 1 g/l of streptomycin for 6 hours at 29° C. Then, 0.1 ml of obtained culture was inoculated into 2 ml of fermentation medium in 20×200 mm test tube and cultivated for 65 hours at 29° C. with a rotary shaker (350 rpm). After the cultivation, the amount of histidine which had accumulated in the medium was determined by paper chromatography. The paper was developed with a mobile phase: n-butanol:acetic acid:water=4:1:1 (v/v). A solution of ninhydrin (0.5%) in acetone was used as a visualizing reagent.

The composition of the fermentation medium (pH 6.0) (g/l) is as follows:

| | |
|---|---|
| Glucose | 100.0 |
| Mameno (soybean protein hydrolysate) | 0.2 of TN (total nitrogen) |
| L-proline | 1.0 |
| (NH$_4$)$_2$SO$_4$ | 25.0 |
| KH$_2$PO$_4$ | 2.0 |
| MgSO$_4$.7H$_2$0 | 1.0 |
| FeSO$_4$.7H$_2$0 | 0.01 |
| MnSO$_4$ | 0.01 |
| Thiamine | 0.001 |
| Betaine | 2.0 |
| CaCO$_3$ | 60.0 |
| Streptomycin | 1.0 |

Glucose, proline, betaine and CaCO$_3$ are sterilized separately. The pH is adjusted to 6.0 before sterilization.

The obtained data are presented in the Table 1.

TABLE 1

| *E. coli* strain | OD$_{450}$ | Amount of histidine, g/l | Yield per glucose, % |
|---|---|---|---|
| 80 (VKPM B-7270) | 14.4 | 10.3 | 11.7 |
| 80/pMW-P$_R$-purH | 15.8 | 14.2 | 15.7 |
| 80::P$_R$-purH | 18.6 | 13.0 | 14.2 |

For mini-jar batch-fermentation, one loop of each strain 80 and 80::P$_R$-purH grown on L-agar was transferred to L-broth and cultivated at 30° C. with rotation (140 rpm) to reach an optical density of OD$_{50}$≈2.0. Then 25 ml of seed culture was added to 250 ml of medium for fermentation and cultivated at 29° C. with rotation (1500 rpm). The duration of the batch-fermentation was approximately 35-40 hours. After the cultivation the amount of histidine which had accumulated in the medium was determined by paper chromatography as described above.

The composition of the jar-fermentation medium (pH 6.0) (g/l) is as follows:

| | |
|---|---|
| Glucose | 100.0 |
| Mameno | 0.2 of TN |
| (NH$_4$)$_2$SO$_4$ | 8.0 |
| KH$_2$PO$_4$ | 1.0 |
| MgSO$_4$.7H$_2$0 | 0.4 |
| FeSO$_4$.7H$_2$0 | 0.02 |
| MnSO$_4$ | 0.02 |
| Thiamine | 0.001 |
| Betaine | 2.0 |
| L-proline | 0.8 |
| L-glutamate | 3.0 |
| L-aspartate | 1.0 |
| Adenosine | 0.1 |

The obtained data are presented in the Table 2.

TABLE 2

| Strain | OD$_{450}$ | Amount of histidine, g/l | Yield per glucose, % |
|---|---|---|---|
| 80 (VKPM B-7270) | 35.0 | 17.3 | 18.0 |
| 80::P$_R$-purH | 22.8 | 19.6 | 20.3 |

It can be seen from the Tables 1 and 2 that enhanced expression of purH gene improved histidine production by the E. coli strain 80.

While the invention has been described in detail with reference to preferred embodiments thereof, it will be apparent to one skilled in the art that various changes can be made, and equivalents employed, without departing from the scope of the invention. Each of the aforementioned documents, as well as the foreign priority document, RU2003126290, is incorporated by reference herein in its entirety.

---

We claim:

1. An isolated L-histidine producing bacterium of the Enterobacteriaceae family which has been modified to have enhanced activity of *Escherichia* AICAR transformylase-IMP cyclohydrolase as compared to said bacterium of the Enterobacteriaceae family which is non-modified, wherein said activity is enhanced by increasing the expression of the AICAR transformylase-IMP cyclohydrolase gene by a method selected from the group consisting of:

(a) increasing the copy number of the AICAR transformylase-IMP cyclohydrolase gene, and (b) placing the AICAR transformylase-IMP cyclohydrolase gene under the control of a more potent promoter instead of the native promoter; and wherein said bacterium is able to produce not less than 1.0 g/L of L-histidine, wherein said L-histidine producing bacterium expresses a gene encoding ATP phosphoribosyl transferase which is desensitized to feedback inhibition by L-histidine, and wherein said AICAR transformylase-IMP cyclohydrolase gene encodes a protein selected from the group consisting of:
(A) a protein comprising the amino acid sequence shown in SEQ ID NO: 2; and
(B) a protein variant of the amino acid sequence shown in SEQ ID NO: 2 wherein said variant is at least 95% homologous with SEQ ID NO: 2 and has AICAR transformylase-IMP cyclohydrolase activity.

2. The bacterium according to claim 1, wherein said bacterium belongs to the genus *Escherichia*.

3. The bacterium according to claim 2, wherein said AICAR transformylase-IMP cyclohydrolase gene copy number is increased by transformation of said bacterium with a multi-copy vector expressing said AICAR transformylase-IMP cyclohydrolase gene.

4. The bacterium according to claim 2, wherein said AICAR transformylase-IMP cyclohydrolase gene copy number is increased by integration of additional copies of said AICAR transformylase-IMP cyclohydrolase gene into the chromosome of said bacterium.

5. The bacterium according to claim 1, wherein said AICAR transformylase-IMP cyclohydrolase gene is selected from the group consisting of:
(a) a DNA comprising the nucleotide sequence of nucleotides 1 to 1590 in SEQ ID NO: 1; and
(b) a DNA which is hybridizable with the full length complement of the nucleotide sequence of nucleotides 1-1590 in SEQ ID NO:1 under stringent conditions, wherein said conditions allow for hybridization of DNA which are not less than 95% identical to the nucleotides 1-1590 in SEQ ID NO: 1, and wherein said DNA encodes a protein having AICAR transformylase-IMP cyclohydrolase activity.

6. A method for producing L-histidine, comprising cultivating the bacterium according to claim 1 in a culture medium, and collecting L-histidine from the culture medium.

7. A method for producing L-histidine comprising cultivating the bacterium of claim 2 in a culture medium, and collecting L-histidine from the culture medium.

8. A method for producing L-histidine, comprising cultivating the bacterium according to claim 3 in a culture medium, and collecting L-histidine from the culture medium.

9. A method for producing L-histidine, comprising cultivating the bacterium according to claim 4 in a culture medium, and collecting L-histidine from the culture medium.

10. A method for producing L-histidine, comprising cultivating the bacterium according to claim 5 in a culture medium, and collecting L-histidine from the culture medium.

* * * * *

SEQUENCE LISTING

```
<160> NUMBER OF SEQ ID NOS: 5

<210> SEQ ID NO 1
<211> LENGTH: 1590
<212> TYPE: DNA
<213> ORGANISM: Escherichia coli
<220> FEATURE:
<221> NAME/KEY: CDS
<222> LOCATION: (1)..(1590)

<400> SEQUENCE: 1 atg caa caa cgt cgt cca gtc cgc cgc gct ctg ctc agt gtt tct gac      48
Met Gln Gln Arg Arg Pro Val Arg Arg Ala Leu Leu Ser Val Ser Asp
  1               5                  10                  15 aaa gcc ggt atc gtc gaa ttc gcc cag gca ctt tcc gca cgc ggt gtg      96
Lys Ala Gly Ile Val Glu Phe Ala Gln Ala Leu Ser Ala Arg Gly Val
                 20                  25                  30 gag ctg ctg tct aca ggg ggc act gcc gtt ctg tta gca gaa aaa ggt     144
Glu Leu Leu Ser Thr Gly Gly Thr Ala Arg Leu Leu Ala Glu Lys Gly
             35                  40                  45 ctg ccg gta acc gaa gtt tcc gat tac acc ggt ttc ccg gag atg atg     192
Leu Pro Val Thr Glu Val Ser Asp Tyr Thr Gly Phe Pro Glu Met Met
         50                  55                  60 gat gga cgc gtg aag acc ctg cat ccg aaa gta cat ggt ggc att ctg     240
Asp Gly Arg Val Lys Thr Leu His Pro Lys Val His Gly Gly Ile Leu
 65                  70                  75                  80 ggc cgt cgc ggc cag gac gat gcc att atg gaa gaa cat cag atc cag     288
Gly Arg Arg Gly Gln Asp Asp Ala Ile Met Glu Glu His Gln Ile Gln
                 85                  90                  95 cct atc gat atg gtg gtt gtt aac ctg tat ccg ttc gcc cag acc gtg     336
Pro Ile Asp Met Val Val Val Asn Leu Tyr Pro Phe Ala Gln Thr Val
            100                 105                 110 gcc cgt gaa ggt tgc tcg ctg gaa gat gcg gtt gag aac atc gat atc     384
Ala Arg Glu Gly Cys Ser Leu Glu Asp Ala Val Glu Asn Ile Asp Ile
        115                 120                 125 ggc ggc cca acg atg gtg cgc tcc gcc gcc aag aac cat aaa gat gtc     432
Gly Gly Pro Thr Met Val Arg Ser Ala Ala Lys Asn His Lys Asp Val
    130                 135                 140 gca atc gtg gtg aag agc agc gac tat gac gcc att att aaa gag atg     480
Ala Ile Val Val Lys Ser Ser Asp Tyr Asp Ala Ile Ile Lys Glu Met
145                 150                 155                 160 gat gac aac gaa gga tcg ctg acg ctt gca acc cgt ttc gac ctc gcc     528
Asp Asp Asn Glu Gly Ser Leu Thr Leu Ala Thr Arg Phe Asp Leu Ala
                165                 170                 175 atc aaa gcc ttc gaa cac act gcc gcc tac gac agc atg att gcc aac     576
Ile Lys Ala Phe Glu His Thr Ala Ala Tyr Asp Ser Met Ile Ala Asn
            180                 185                 190 tac ttc ggc agc atg gtt ccg gct tac cac ggt gaa agc aaa gaa gcc     624
Tyr Phe Gly Ser Met Val Pro Ala Tyr His Gly Glu Ser Lys Glu Ala
        195                 200                 205 gcc ggt cgc ttc cca cgc acg ctg aac ctg aac ttc att aag aag ctg     672
Ala Gly Arg Phe Pro Arg Thr Leu Asn Leu Asn Phe Ile Lys Lys Leu
    210                 215                 220 gat atg cgt tac ggc gag aac agc cac cag cag gct gcc ttc tat ata     720
```

-continued

| | | |
|---|---|---|
| Asp Met Arg Tyr Gly Glu Asn Ser His Gln Gln Ala Ala Phe Tyr Ile<br>225                            230                           235                           240 | |
| gaa gag aat gtg aaa gaa gcc tcc gtt gct acc gca acc cag gtt cag<br>Glu Glu Asn Val Lys Glu Ala Ser Val Ala Thr Ala Thr Gln Val Gln<br>                      245                          250                         255 | 768 |
| ggt aaa gcc ctc tct tat aac aac atc gcc gat acc gat gcg gcg ctg<br>Gly Lys Ala Leu Ser Tyr Asn Asn Ile Ala Asp Thr Asp Ala Ala Leu<br>                260                           265                         270 | 816 |
| gag tgc gtg aaa gag ttc gcc gag ccg gca tgt gtg att gtg aag cac<br>Glu Cys Val Lys Glu Phe Ala Glu Pro Ala Cys Val Ile Val Lys His<br>            275                        280                        285 | 864 |
| gcc aac cct tgc ggc gtg gct atc ggc aat tcc att ctt gat gct tac<br>Ala Asn Pro Cys Gly Val Ala Ile Gly Asn Ser Ile Leu Asp Ala Tyr<br>        290                        295                        300 | 912 |
| gat cgc gcg tac aaa acc gac cca acc tcc gca ttc ggc ggc atc att<br>Asp Arg Ala Tyr Lys Thr Asp Pro Thr Ser Ala Phe Gly Gly Ile Ile<br>305                            310                           315                           320 | 960 |
| gcc ttt aac cgc gag ctg gat gcg gaa acc gca cag gcc atc att tct<br>Ala Phe Asn Arg Glu Leu Asp Ala Glu Thr Ala Gln Ala Ile Ile Ser<br>                325                           330                         335 | 1008 |
| cgt cag ttt gtc gaa gtg att att gcg ccg tcc gcc agc gaa gaa gcc<br>Arg Gln Phe Val Glu Val Ile Ile Ala Pro Ser Ala Ser Glu Glu Ala<br>            340                        345                        350 | 1056 |
| ctg aaa atc acc gcc gcc aaa cag aac gta cgc gtt ctg acc tgc ggt<br>Leu Lys Ile Thr Ala Ala Lys Gln Asn Val Arg Val Leu Thr Cys Gly<br>                355                           360                         365 | 1104 |
| cag tgg ggc gag cgt gtt ccg ggc ctc gat ttc aaa cgc gtg aac ggc<br>Gln Trp Gly Glu Arg Val Pro Gly Leu Asp Phe Lys Arg Val Asn Gly<br>370                            375                           380 | 1152 |
| ggt ctg ctg gtt cag gat cgt gac ctg ggg atg gtc ggt gcg gaa gaa<br>Gly Leu Leu Val Gln Asp Arg Asp Leu Gly Met Val Gly Ala Glu Glu<br>385                            390                           395                           400 | 1200 |
| ctg cgc gtg gtg acc aaa cgt cag ccg agc gaa cag gaa ctg cgt gat<br>Leu Arg Val Val Thr Lys Arg Gln Pro Ser Glu Gln Glu Leu Arg Asp<br>                          405                           410                         415 | 1248 |
| gcg ctg ttc tgc tgg aag gtg gcg aag ttt gtg aaa tcc aac gct atc<br>Ala Leu Phe Cys Trp Lys Val Ala Lys Phe Val Lys Ser Asn Ala Ile<br>                420                           425                        430 | 1296 |
| gtc tat gcc aaa aac aat atg act atc ggc att ggc gcg ggc cag atg<br>Val Tyr Ala Lys Asn Asn Met Thr Ile Gly Ile Gly Ala Gly Gln Met<br>                      435                          440                         445 | 1344 |
| agc cgc gtg tac tcc gca aaa atc gcc ggt att aaa gcg gcc gat gaa<br>Ser Arg Val Tyr Ser Ala Lys Ile Ala Gly Ile Lys Ala Ala Asp Glu<br>        450                        455                        460 | 1392 |
| ggc ctg gaa gtg aaa ggt tcc tcg atg gct tct gac gcg ttc ttc ccg<br>Gly Leu Glu Val Lys Gly Ser Ser Met Ala Ser Asp Ala Phe Phe Pro<br>465                            470                           475                           480 | 1440 |
| ttc cgc gac ggt att gat gcc gcc gcc gct gcg ggc gtg acc tgc gta<br>Phe Arg Asp Gly Ile Asp Ala Ala Ala Ala Ala Gly Val Thr Cys Val<br>                      485                           490                         495 | 1488 |
| atc cag cct ggc ggt tct atc cgt gat gac gaa gtg att gcc gcc gcc<br>Ile Gln Pro Gly Gly Ser Ile Arg Asp Asp Glu Val Ile Ala Ala Ala<br>                        500                           505                        510 | 1536 |
| gac gag cac ggt att gcg atg ctc ttc acc gac atg cgc cac ttc cgc<br>Asp Glu His Gly Ile Ala Met Leu Phe Thr Asp Met Arg His Phe Arg<br>            515                        520                        525 | 1584 |
| cat taa<br>His | 1590 |

-continued

```
<210> SEQ ID NO 2
<211> LENGTH: 529
<212> TYPE: PRT
<213> ORGANISM: Escherichia coli

<400> SEQUENCE: 2

Met Gln Gln Arg Arg Pro Val Arg Arg Ala Leu Leu Ser Val Ser Asp
 1               5                  10                  15

Lys Ala Gly Ile Val Glu Phe Ala Gln Ala Leu Ser Ala Arg Gly Val
             20                  25                  30

Glu Leu Leu Ser Thr Gly Gly Thr Ala Arg Leu Leu Ala Glu Lys Gly
         35                  40                  45

Leu Pro Val Thr Glu Val Ser Asp Tyr Thr Gly Phe Pro Glu Met Met
     50                  55                  60

Asp Gly Arg Val Lys Thr Leu His Pro Lys Val His Gly Gly Ile Leu
 65                  70                  75                  80

Gly Arg Arg Gly Gln Asp Asp Ala Ile Met Glu Glu His Gln Ile Gln
                 85                  90                  95

Pro Ile Asp Met Val Val Val Asn Leu Tyr Pro Phe Ala Gln Thr Val
            100                 105                 110

Ala Arg Glu Gly Cys Ser Leu Glu Asp Ala Val Glu Asn Ile Asp Ile
        115                 120                 125

Gly Gly Pro Thr Met Val Arg Ser Ala Ala Lys Asn His Lys Asp Val
130                 135                 140

Ala Ile Val Val Lys Ser Ser Asp Tyr Asp Ala Ile Ile Lys Glu Met
145                 150                 155                 160

Asp Asp Asn Glu Gly Ser Leu Thr Leu Ala Thr Arg Phe Asp Leu Ala
                165                 170                 175

Ile Lys Ala Phe Glu His Thr Ala Ala Tyr Asp Ser Met Ile Ala Asn
            180                 185                 190

Tyr Phe Gly Ser Met Val Pro Ala Tyr His Gly Glu Ser Lys Glu Ala
        195                 200                 205

Ala Gly Arg Phe Pro Arg Thr Leu Asn Leu Asn Phe Ile Lys Lys Leu
    210                 215                 220

Asp Met Arg Tyr Gly Glu Asn Ser His Gln Gln Ala Ala Phe Tyr Ile
225                 230                 235                 240

Glu Glu Asn Val Lys Glu Ala Ser Val Ala Thr Ala Thr Gln Val Gln
                245                 250                 255

Gly Lys Ala Leu Ser Tyr Asn Asn Ile Ala Asp Thr Asp Ala Ala Leu
            260                 265                 270

Glu Cys Val Lys Glu Phe Ala Glu Pro Ala Cys Val Ile Val Lys His
        275                 280                 285

Ala Asn Pro Cys Gly Val Ala Ile Gly Asn Ser Ile Leu Asp Ala Tyr
    290                 295                 300

Asp Arg Ala Tyr Lys Thr Asp Pro Thr Ser Ala Phe Gly Gly Ile Ile
305                 310                 315                 320

Ala Phe Asn Arg Glu Leu Asp Ala Glu Thr Ala Gln Ala Ile Ile Ser
                325                 330                 335

Arg Gln Phe Val Glu Val Ile Ile Ala Pro Ser Ala Ser Glu Glu Ala
            340                 345                 350

Leu Lys Ile Thr Ala Ala Lys Gln Asn Val Arg Val Leu Thr Cys Gly
        355                 360                 365

Gln Trp Gly Glu Arg Val Pro Gly Leu Asp Phe Lys Arg Val Asn Gly
    370                 375                 380
```

-continued

```
Gly Leu Leu Val Gln Asp Arg Asp Leu Gly Met Val Gly Ala Glu Glu
385                 390                 395                 400

Leu Arg Val Val Thr Lys Arg Gln Pro Ser Glu Gln Glu Leu Arg Asp
                405                 410                 415

Ala Leu Phe Cys Trp Lys Val Ala Lys Phe Val Lys Ser Asn Ala Ile
                420                 425                 430

Val Tyr Ala Lys Asn Asn Met Thr Ile Gly Ile Gly Ala Gly Gln Met
                435                 440                 445

Ser Arg Val Tyr Ser Ala Lys Ile Ala Gly Ile Lys Ala Ala Asp Glu
            450                 455                 460

Gly Leu Glu Val Lys Gly Ser Ser Met Ala Ser Asp Ala Phe Phe Pro
465                 470                 475                 480

Phe Arg Asp Gly Ile Asp Ala Ala Ala Ala Gly Val Thr Cys Val
                485                 490                 495

Ile Gln Pro Gly Gly Ser Ile Arg Asp Asp Glu Val Ile Ala Ala Ala
                500                 505                 510

Asp Glu His Gly Ile Ala Met Leu Phe Thr Asp Met Arg His Phe Arg
            515                 520                 525

His

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 3
ttttaagctt cacgtaacgc tctctgtaa                                      29

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 4
tttttctaga ttaatggcgg aagtggcg                                       28

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
cgcgcttcaa atgaaacaga t                                              21
```